(12) United States Patent
Yoshimura

(10) Patent No.: US 9,410,872 B2
(45) Date of Patent: Aug. 9, 2016

(54) EXHAUST GAS FLOWMETER AND EXHAUST GAS ANALYZING SYSTEM

(71) Applicant: HORIBA, Ltd., Kyoto (JP)

(72) Inventor: Tomoshi Yoshimura, Kyoto (JP)

(73) Assignee: Horiba, Ltd., Kyoto (JP)

( * ) Notice: Subject to any disclaimer, the term of this patent is extended or adjusted under 35 U.S.C. 154(b) by 161 days.

(21) Appl. No.: 14/278,298

(22) Filed: May 15, 2014

(65) Prior Publication Data

US 2014/0338540 A1 Nov. 20, 2014

(30) Foreign Application Priority Data

May 16, 2013 (JP) .................................. 2013-104434

(51) Int. Cl.
| | |
|---|---|
| *G01F 9/00* | (2006.01) |
| *G01N 1/22* | (2006.01) |
| *G01N 21/3504* | (2014.01) |
| *G01F 1/704* | (2006.01) |
| *G01N 21/3554* | (2014.01) |
| *G01M 15/10* | (2006.01) |
| *G01N 21/61* | (2006.01) |

(52) U.S. Cl.
CPC .............. *G01N 1/2252* (2013.01); *G01F 1/704* (2013.01); *G01F 9/00* (2013.01); *G01M 15/108* (2013.01); *G01N 21/3504* (2013.01); *G01N 21/3554* (2013.01); *F01N 2560/07* (2013.01); *G01N 21/61* (2013.01); *G01N 2001/2255* (2013.01)

(58) Field of Classification Search
CPC ......... F01N 13/008; G01F 1/46; G01F 9/001; G01M 15/102; G01M 15/106

USPC ......... 55/385.1, 385.3, DIG. 34; 96/417, 420, 96/422; 73/23.31, 114.69, 114.71, 114.76
See application file for complete search history.

(56) References Cited

U.S. PATENT DOCUMENTS

| | | | |
|---|---|---|---|
| 5,968,452 A | 10/1999 | Silvis | |
| 6,470,732 B1 * | 10/2002 | Breton | ................... F01N 13/008 73/114.69 |

(Continued)

FOREIGN PATENT DOCUMENTS

| | | |
|---|---|---|
| EP | 2339156 A2 | 6/2011 |
| JP | 62-005151 A | 7/1985 |
| JP | 2004117259 A | 4/2004 |

OTHER PUBLICATIONS

Wiers, Ward W., et al. Carbon Dioxide (CO2) Tracer Technique for Model Mass Exhaust Emission Measurement, SAE Technical Paper 720126, Feb. 1, 1972, XP002729129, New York, pp. 1-14.

*Primary Examiner* — Duane Smith
*Assistant Examiner* — Minh-Chau Pham
(74) *Attorney, Agent, or Firm* — Brooks Kushman P.C.

(57) ABSTRACT

The present invention is adapted to be provided with: a first sampling line for sampling raw exhaust gas; a first concentration measuring part that measures the concentration of the predetermined target component contained in the raw exhaust gas; a second sampling line for sampling diluted exhaust gas; a second concentration measuring part that measures the concentration of the target component contained in the diluted exhaust gas; and an arithmetic unit that, with use of first measured concentration, second measured concentration, and a diluted exhaust gas flow rate, calculates a raw exhaust gas flow rate, wherein in a state where the first sampling line and the first concentration measuring part are heated, the first concentration measuring part measures the concentration of the target component contained in the raw exhaust gas.

4 Claims, 2 Drawing Sheets

(56) References Cited

U.S. PATENT DOCUMENTS

2004/0064243 A1* 4/2004 Nakamura ............ F01N 13/008
  701/114

2007/0254374 A1* 11/2007 Iharada .............. G01N 33/1846
  436/146

* cited by examiner

EXHAUST GAS FLOWMETER AND EXHAUST GAS ANALYZING SYSTEM

CROSS-REFERENCE TO RELATED APPLICATION

This application claims priority to JP Application No. 2013-104434, filed May 16, 2013, the disclosure of which is incorporated in its entirety by reference herein.

TECHNICAL FIELD

The present invention relates to an exhaust gas flowmeter that employs a tracer method to measure a flow rate of exhaust gas emitted from an internal combustion engine, and to an exhaust gas analyzing system using the exhaust gas flowmeter.

BACKGROUND ART

In the past, as an exhaust gas analyzing system based on a dilution sampling method that dilutes exhaust gas emitted from an internal combustion engine, there has been a system provided with: a main flow path through which exhaust gas emitted from an exhaust pipe of an internal combustion engine flows; a diluent gas flow path that meets the main flow path, through which diluent gas for diluting the exhaust gas flows; and a flow rate control part that is provided on a downstream side of a meeting point between the main flow path and the diluent gas flow path to control a flow rate of diluted exhaust gas produced by diluting the exhaust gas with the diluent gas.

In the dilution sampling method, as one of meters for measuring a flow rate of the exhaust gas emitted from an exhaust pipe, an exhaust gas flowmeter that performs measurement by a tracer method is known.

The exhaust gas flowmeter is, for example, as disclosed in JP-A-62-5151, provided with: a sampling line for, from a main flow path on an upstream side of a meeting point, sampling raw exhaust gas that is exhaust gas before dilution; a sampling line for, from the main flow path on a downstream side of the meeting point, sampling diluted exhaust gas that is the exhaust gas after the dilution; concentration meters that are connected to the respective sampling lines to measure concentrations of target components (such as CO2) contained in the sampled gases; and an arithmetic unit that calculates a flow rate of the raw exhaust gas from the target component concentrations measured by the respective concentration meters, and a diluted exhaust gas flow rate controlled by a flow rate control part.

According to the exhaust gas flowmeter configured as described, the respective concentration meters instantaneously measure the concentrations of the target components contained in the raw exhaust gas and the diluted exhaust gas, and thereby the flow rate of the raw exhaust gas can be instantaneously measured on the assumption that a ratio between the concentrations is equal to a ratio of the dilution by diluent gas.

Meanwhile, exhaust gas emitted from an internal combustion engine contains large amounts of components acting as interference components such as moisture. Methods for removing the moisture include a method that provides a drain separator between a sampling line and a concentration meter to remove the moisture contained in the exhaust gas, and then introduces the exhaust gas into the concentration meter (so-called Dry measurement). In this case, the concentration of a target component is increased as compared with that in a state where the exhaust gas contains the moisture, and therefore on the basis of a conversion expression (Dry to Wet conversion expression) provided in the regulation (40 CFR Part 1065), the concentration is converted to the concentration of the target component contained in the exhaust gas immediately after the emission from the internal combustion engine.

However, in practice, during a period when the exhaust gas emitted from the internal combustion engine flows through an exhaust pipe, the moisture contained in the exhaust gas may be condensed or adsorbed in the exhaust pipe. In this case, between the exhaust gas immediately after the emission from the internal combustion engine and the exhaust gas (the above-described raw exhaust gas) emitted from the exhaust pipe, a difference in contained moisture amount occurs, and the concentration of the target component as a result of the conversion by the conversion expression does not indicate the concentration of the target component contained in the raw exhaust gas. Also, it is difficult to know how much the condensation, adsorption, or the like occurs in the exhaust pipe, and therefore it is difficult to accurately measure the concentration of the target component contained in the raw exhaust gas.

On the other hand, a method that, without using a drain separator, measures the concentration of the target component in a state where the exhaust gas emitted from the exhaust pipe contains the moisture (so-called Wet measurement) is also possible; however, in this method, in the sampling line or concentration meter through which the raw exhaust gas particularly containing a large amount of moisture flows, the moisture contained in the raw exhaust gas is condensed or adsorbed. In the case where the target component is a component having solubility, such as CO2, this may cause a measurement error because the target component is dissolved in the condensed or adsorbed moisture, and even in this case, there occurs a problem of being unable to accurately measure the concentration of the target component.

SUMMARY OF INVENTION

Technical Problem

Therefore, a main desired object of the present invention is to accurately measure the concentration of a target component contained in, in particular, exhaust gas before dilution, and thereby improve accuracy of exhaust gas flow rate measurement by a tracer method.

Solution to Problem

That is, an exhaust gas flowmeter according to the present invention is one used for an exhaust gas dilution system provided with: a main flow path through which exhaust gas emitted from an internal combustion engine flows; and a diluent gas flow path that meets the main flow path, through which diluent gas for diluting the exhaust gas flows, and provided with: a first sampling line for, from an upstream side of a meeting point between the main flow path and the diluent gas flow path in the main flow path, sampling raw exhaust gas that is the exhaust gas before the dilution; a first concentration measuring part that is provided in the first sampling line to measure concentration of a predetermined target component contained in the raw exhaust gas; a second sampling line for, from a downstream side of the meeting point in the main flow path, sampling diluted exhaust gas that is the exhaust gas after the dilution; a second concentration measuring part that is provided in the second sampling line to measure concentration of the target component contained in the diluted exhaust gas; and an arithmetic unit that, with use of first measured concentration obtained by the first concentration measuring part, second measured concentration obtained by the second concentration measuring part, and a diluted exhaust gas flow rate that is a flow rate of the diluted exhaust gas, calculates a raw exhaust gas flow rate that is a flow rate of the raw exhaust gas, wherein in a state where the first sampling line and the first concentration measuring part are heated, the first concentration measuring part measures the concentration of the target component contained in the raw exhaust gas.

If so, the concentration of the target component is measured in the state where the first sampling line and the first concentration measuring part are heated, and therefore condensation, adsorption, or the like of moisture or the like contained in the raw exhaust gas in the first sampling line or the first concentration measuring part can be prevented. In doing so, the raw exhaust gas can be measured in a state of containing the moisture (Wet measurement), so that the target component contained in the raw exhaust gas is not dissolved in the moisture, and therefore the concentration of the target component can be accurately measured to improve accuracy of exhaust gas flow rate measurement by a tracer method.

Also, the concentration of the target component is measured in the state where the raw exhaust gas contains the moisture (Wet measurement), and therefore the need for using a Dry to Wet conversion expression to convert to concentration immediately after the emission from the internal combustion engine is also eliminated.

Further, a drain separator or the like is not used, which enables the sampling line from the main flow path to the first concentration measuring part to be shortened to improve responsiveness of concentration measurement, and in addition, can contribute to reductions in size and weight of the exhaust gas flowmeter.

In general, condensation, adsorption, or the like of moisture contained in diluted exhaust gas is unlikely to occur; however, in order to more accurately measure the concentration of the target component contained in the diluted exhaust gas with more surely preventing condensation, adsorption, or the like of moisture or the like, preferably, in a state where the second sampling line and the second concentration measuring part are heated, the second concentration measuring part measures the concentration of the target component contained in the diluted exhaust gas.

In order to, even in the case where moisture influences the concentration measurement of the target component, accurately measure the concentration of the target component contained in the raw exhaust gas or the diluted exhaust gas, desirably, the heated concentration measuring part is provided with: a moisture concentration meter that measures moisture concentrations in the exhaust gas; and a target component concentration meter that measures moisture-influenced concentration that is concentration of the target component in the exhaust gas in a state of being influenced by moisture, and calculates the concentration of the target component contained in the exhaust gas as concentration that is the moisture-influenced concentration from which an influence of moisture is removed with use of the moisture concentration.

Further, according to an exhaust gas analyzing system using the exhaust gas flowmeter of the present invention, the flow rate of the exhaust gas emitted from the internal combustion engine can be more accurately measured by the tracer method to perform highly accurate exhaust gas analysis.

Advantageous Effects of Invention

According to the present invention configured as described, by accurately measuring the concentration of a target component contained in, in particular, exhaust gas before dilution, accuracy of exhaust gas flow rate measurement by the tracer method can be improved.

DESCRIPTION OF EMBODIMENTS

In the following, an exhaust gas analyzing system 100 using an exhaust gas flowmeter 1 according to the present invention is described with reference to the drawings.

The exhaust gas analyzing system 100 according to the present embodiment is a system based on a dilution sampling method, and also a system that uses an exhaust gas dilution system to dilute exhaust gas emitted from an internal combustion engine 201 such as an engine with diluent gas purified from air several times, and then performs concentration measurement. In the present embodiment, described below is the exhaust gas analyzing system 100 that as the exhaust gas dilution system, uses a constant volume sampling apparatus 101 that samples a total amount of the exhaust gas, and dilutes the exhaust gas with the diluent gas to achieve a constant flow rate.

Figure 1:
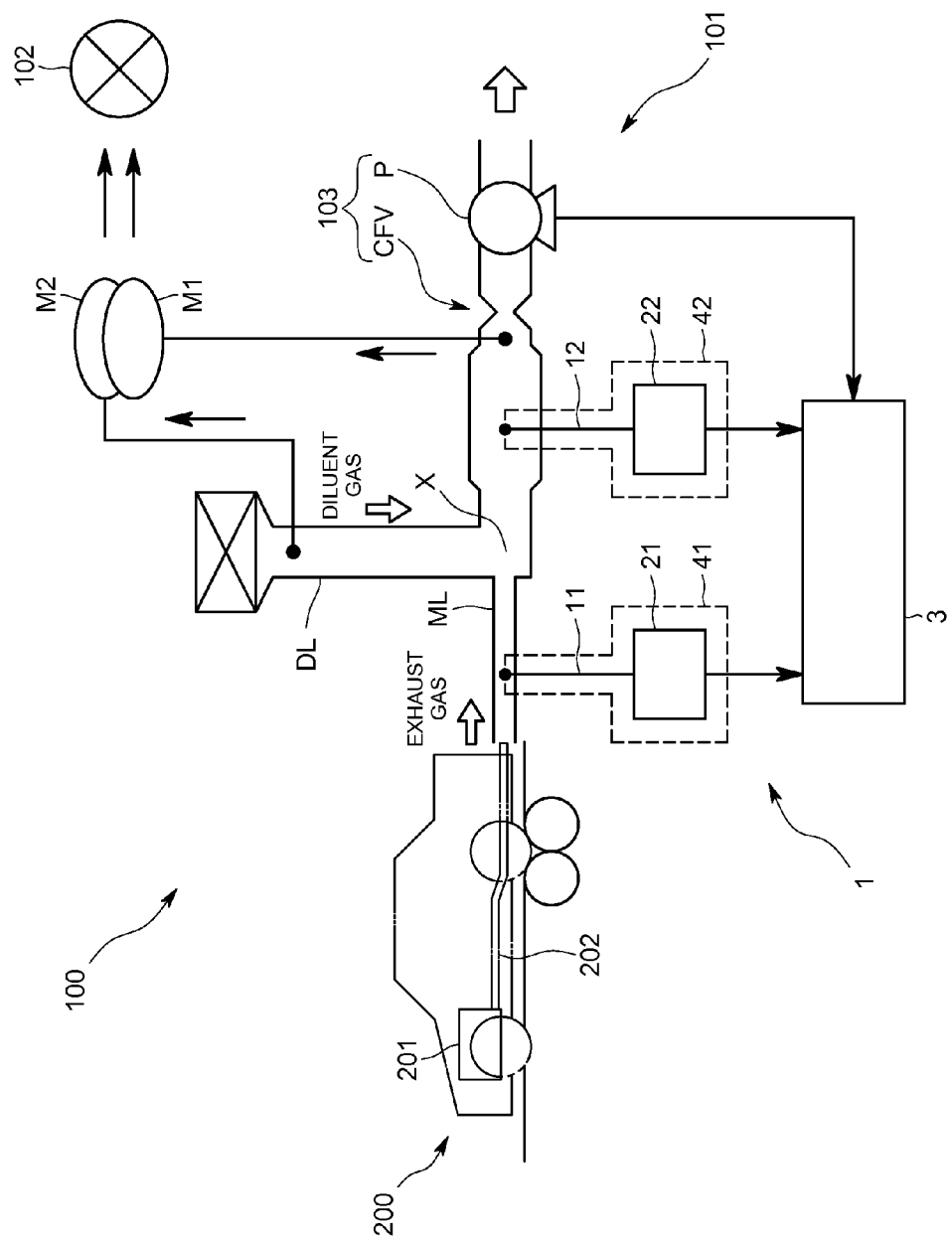
FIG. 1 is a diagram schematically illustrating an exhaust gas flowmeter of the present embodiment.

Specifically, the exhaust gas analyzing system 100 is, as illustrated in FIG. 1, provided with: the constant volume sampling apparatus 101 that constantly controls a total flow rate of the sum of the total amount of the exhaust gas and the diluent gas to a constant flow rate, and collects part of the diluted exhaust gas and part of the diluent gas; an exhaust gas sampling bag M1 that contains the collected exhaust gas; a diluent gas sampling bag M2 that contains the collected diluent gas; and an exhaust gas analyzer 102 that analyzes concentrations of predetermined components (such as HC, CO, or CO2) in the gases collected in the respective sampling bags M1 and M2, and calculates the concentration of the predetermined component contained in the exhaust gas.

The constant volume sampling apparatus 101 is one that is, as illustrated in FIG. 1, provided with: a main flow path ML through which the exhaust gas emitted from an exhaust pipe 202 of the internal combustion engine 201 flows; a diluent gas flow path DL that meets the main flow path ML, through which the diluent gas for diluting the exhaust gas flows; and a flow rate control part 103 that is provided on a downstream side of a meeting point X between the main flow path ML and the diluent gas flow path DL to control a flow rate of the diluted exhaust gas produced by diluting the exhaust gas with the diluent gas to a constant flow rate.

The flow rate control part 103 is one that is, as illustrated in FIG. 1, of a critical flow venturi type including a critical flow venturi CFV and a blower or a suction pump P. In the present embodiment, the one critical flow venturi CFV is provided; however, the present invention may be configured to be able to change the flow rate of the diluted exhaust gas by providing a plurality of critical flow venturis CFV in parallel, and using valves such as on/off valves to change a critical flow venturi CFV where the diluted exhaust gas is to be flowed.

An exhaust gas flowmeter 1 used for the above-described exhaust gas analyzing system 100 is one that measures the concentrations of the target components contained in the exhaust gases before and after the dilution, respectively, to thereby measure a flow rate of the exhaust gas emitted from the exhaust pipe 202 by a tracer method. Note that in the present embodiment, the target component is CO2.

Specifically, the exhaust gas flowmeter 1 is, as illustrated in FIG. 1, provided with: a first sampling line 11 for, from an upstream side of the meeting point X in the main flow path ML, sampling the raw exhaust gas that is the exhaust gas before the dilution; a first concentration measuring part 21 that is connected to the first sampling line 11 to measure the concentration of CO2 contained in the raw exhaust gas, a second sampling line 12 for, from the downstream side of the meeting point X in the main flow path ML, sampling the diluted exhaust gas that is the exhaust gas after the dilution; a second concentration measuring part 22 that is connected to the second sampling line 12 to measure the concentration of CO2 contained in the diluted exhaust gas; and an arithmetic unit 3 that calculates the flow rate of the raw exhaust gas.

The first sampling line 11 is one that is intended to sample the raw exhaust gas to supply the sampled raw exhaust gas to the first concentration measuring part 21, and one end thereof is connected on the upstream side of the meeting point X in the main flow path ML, whereas the other end thereof is connected to the first concentration measuring part 21. In addition, the sampling through the first sampling line 11 is performed by an unillustrated suction pump.

The second sampling line 12 is one that is intended to sample the diluted exhaust gas to supply the sampled diluted exhaust gas to the second concentration measuring part 22, and one end thereof is connected on the downstream side of the meeting point X in the main flow path ML, whereas the other end thereof is connected to the second concentration measuring part 22. In addition, the sampling through the second sampling line 12 is performed by an unillustrated suction pump.

The first concentration measuring part 21 is one that instantaneously measures the concentration of CO2 contained in the supplied raw exhaust gas, whereas the second concentration measuring part 22 is one that instantaneously measures the concentration of CO2 contained in the supplied diluted exhaust gas, and both of them are configured to be able to measure the CO2 concentrations in states where the exhaust gases contain moisture (Wet measurement), respectively.

The concentration measuring parts 21 and 22 are both NDIR analyzers each having a function as a moisture concentration meter that measures moisture concentration in corresponding exhaust gas and a function as a target component concentration meter that measures target component concentration, and have the same configuration.

In the following, as a representative of them, the configuration of the NDIR analyzer used as the first concentration measuring part 21 is described.

Figure 2:
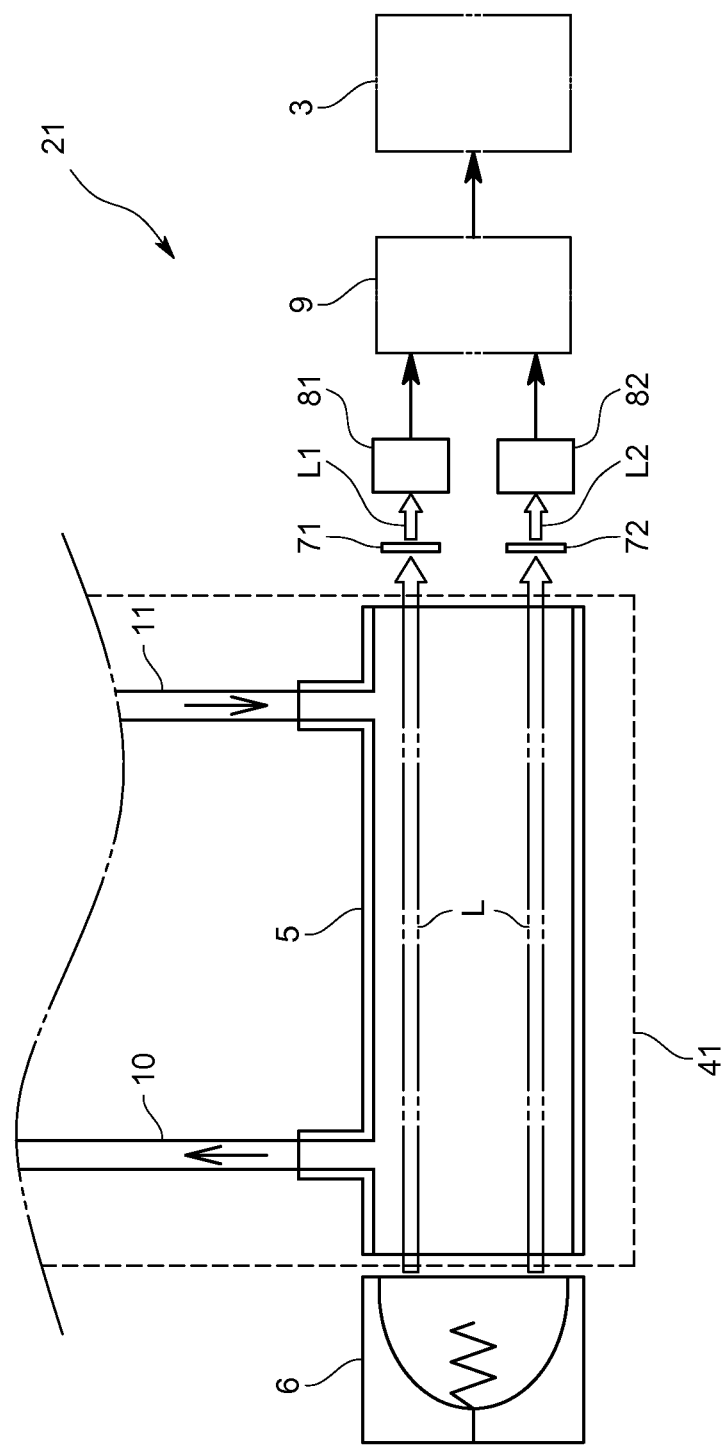
FIG. 2 is a diagram schematically illustrating a configuration of a concentration measuring part in the same embodiment.

The NDIR analyzer used as the first concentration measuring part 21 is one that is, as illustrated in FIG. 2, provided with: a measuring cell 5 that is connected with the sampling line 11 and supplied with the exhaust gas (raw exhaust gas here); an infrared light source 6 that irradiates the measuring cell 5 with infrared light L from outside; a first optical filter 71 that transmits infrared light L1 in a wavelength range corresponding to an absorption spectrum of moisture; a first optical detector 81 that detects optical intensity of the infrared light L1; a second optical filter 72 that transmits infrared light L2 in a wavelength range corresponding to an absorption spectrum of CO2; a second optical detector 82 that detects optical intensity of the infrared light L2; and an actual concentration calculation part 9 that calculates the concentration (actual concentration) of CO2 contained in the exhaust gas, from which an influence of moisture is removed.

In addition, the first concentration measuring part 21 is configured such that the exhaust gas supplied through the sampling line 11 to the measuring cell 5 is discharged through a discharge line 10, and the discharge line 10 may be configured to return the exhaust gas to be discharged to the main flow path ML, or to discharge the exhaust gas outside.

The absorption spectrum of moisture is not influenced by the absorption spectrum of CO2, whereas the absorption spectrum of CO2 is influenced by the absorption spectrum of moisture, and therefore the CO2 absorption spectrum detected by the second optical detector 82 is an absorption spectrum that is detected in a state of being influenced by moisture contained in the exhaust gas.

The actual concentration calculation part 9 obtains an optical intensity signal from the first optical detector 81 to calculate the moisture concentration in the exhaust gas and also obtains an optical intensity signal from the second optical detector 82 to calculate moisture-influenced concentration that is the CO2 concentration influenced by the moisture in the exhaust gas. Then, on the basis of the moisture concentration, the actual concentration calculation part 9 calculates the actual CO2 concentration that is the moisture-influenced concentration from which the influence of the moisture is removed.

The first concentration measuring part 21 configured as described above instantaneously measures the actual concentration $C_{before\_dilution}(t)$ of CO2 contained in the raw exhaust gas supplied through the first sampling line 11, and also transmits a result of the measurement to the arithmetic unit 3.

Similarly, the second concentration measuring part 22 instantaneously measures actual concentration $C_{after\_dilution}(t)$ of CO2 contained in the diluted exhaust gas supplied through the second sampling line 12, and also transmits a result of the measurement to the arithmetic unit 3.

The arithmetic unit 3 is one that obtains signals from the respective concentration measuring parts 21 and 22, and also obtains the diluted exhaust gas flow rate $Q_{mix}$ controlled by the flow rate control part 103 to calculate the raw exhaust gas flow rate $Q_{ex}(t)$. In the present embodiment, the diluted exhaust gas flow rate $Q_{mix}$ is a critical flow rate of the critical flow venturi CFV.

In addition, the arithmetic unit 3 is a dedicated or general-purpose computer having an unillustrated CPU, memory, input/output interface, AD converter, and the like.

To describe this in detail, the arithmetic unit 3 is configured to calculate a concentration ratio ($=C_{after\_dilution}(t)/C_{before\_dilution}(t)$) of the actual concentration $C_{after\_dilution}(t)$ of CO2 contained in the diluted exhaust gas, which is obtained by the second concentration measuring part 22, to the actual concentration $C_{before\_dilution}(t)$ of CO2 contained in the raw exhaust gas, which is obtained by the first concentration measuring part 21, and multiply the diluted exhaust gas flow rate $Q_{mix}$ by the concentration ratio to instantaneously calculate the raw exhaust gas flow rate $Q_{ex}(t)$ ($=Q_{mix} \times C_{after\_dilution}(t)/C_{before\_dilution}(t)$).

Also, the arithmetic unit 3 in the present embodiment is configured to use the raw exhaust gas flow rate $Q_{ex}(t)$ to calculate instantaneous exhaust gas mass $MX(t)$ of the predetermined measuring component X (such as HC, CO, or CO2) that is contained in the exhaust gas and discharged from the exhaust pipe 202.

To describe this in detail, the arithmetic unit 3 is configured to obtain the exhaust gas concentration $CX(t)$ of the measuring component X contained in the raw exhaust gas from the above-described first concentration measuring part 21, and also multiply the above-described raw exhaust gas flow rate Qex(t) by the exhaust gas concentration CX(t) and preliminarily stored density pX of the measuring component X to calculate the instantaneous exhaust gas mass MX(t) (=Qex(t)×CX(t)×pX) of the predetermined measuring component X.

Further, in the present embodiment, as illustrated in FIGS. 1 and 2, a first heating mechanism 41 that heats the first sampling line 11 and the first concentration measuring part 21, and a second heating mechanism 42 that heats the second sampling line 12 and the second concentration measuring part 22 are provided.

In addition, in the present embodiment, the heating mechanisms 41 and 42 are configured to be able to operate independently of each other.

The first heating mechanism 41 is one that is provided with, for example, an unillustrated heater, and heats at least the first sampling line 11 and the measuring cell 5 of the first concentration measuring part 21 to keep a desired setting temperature.

The second heating mechanism 42 is also one that is provided with, for example, an unillustrated heater, and heats at least the second sampling line 12 and the measuring cell 5 of the second concentration measuring part 22 to keep a desired setting temperature.

The setting temperatures of the heating mechanisms 41 and 42 are set to, for example, 80° C. at which the moisture contained in the raw exhaust gas and the moisture contained in the diluted exhaust gas are not condensed in the respective sampling lines 11 and 12 or the respective concentration measuring parts 21 and 22.

In addition, in the case where a condensable component having a high boiling point is contained in the exhaust gas, the setting temperatures may be set to a higher temperature, and in the case where NH3 or the like adsorbable to the sampling line 11 or 12 is contained in the exhaust gas, the setting temperatures may be set to a temperature at which NH3 or the like is not adsorbed.

Also, heating times by the heating mechanisms 41 and 42 may be set to times from the starts of sampling the exhaust gases through the sampling lines 11 and 12 to the ends of measuring the target component concentrations by the concentration measuring parts 21 and 22, or heating temperatures may be regulated to the predetermined temperature before the starts of the sampling, respectively.

According to the exhaust gas flowmeter 1 according to the present embodiment configured as described above, the first heating mechanism 41 heats the first sampling line 11 and the first concentration measuring part 21 during a period from the start of sampling the raw exhaust gas to the end of measuring the concentration of CO2 contained in the raw exhaust gas, and therefore without condensation or adsorption of the moisture in the first sampling line 11 or the first concentration measuring part 21 during the period, the raw exhaust gas can be measured in the state of containing the moisture (Wet measurement). This prevents CO2 contained in the raw exhaust gas from being dissolved in the moisture, and therefore enables the CO2 concentration to be accurately obtained to improve accuracy of the exhaust gas flow rate measurement by the tracer method.

Also, the CO2 concentration is measured in the state where the raw exhaust gas contains the moisture (Wet measurement), and therefore without the need for using the Dry to Wet conversion expression to convert to the concentration immediately after the emission from the internal combustion engine 201, the concentration of the target component in the exhaust gas emitted from the internal combustion engine through the exhaust pipe can be accurately measured.

Further, in general, condensation, adsorption, or the like of moisture contained in diluted exhaust gas is unlikely to occur; however, the CO2 concentration is measured with the second sampling line 12 and the second concentration measuring part 22 being heated as well, and therefore the concentration of CO2 contained in the diluted exhaust gas can be accurately measured with the moisture contained in the diluted exhaust gas being more surely prevented from being condensed or adsorbed.

In addition, a drain separator or the like is not used, which enables the sampling lines 11 and 12 from the main flow path ML to the concentration measuring parts 21 and 22 to be shortened to improve responsiveness of concentration measurement, and in addition, can contribute to reductions in size and weight of the exhaust gas flowmeter 1.

Still in addition, the first heating mechanism 41 and the second heating mechanism 42 are configured to be able to operate independently of each other, and therefore in the case where heating by the second heating mechanism 42 is unnecessary, operating only the first heating mechanism 41 leads to electricity saving and energy saving.

In the case of using an NDIR method to measure CO2 concentration in exhaust gas, in the past, the measurement has been influenced by moisture contained in the exhaust gas; however, each of the concentration measuring parts 21 and 22 according to the present embodiment has the function as a moisture concentration meter and the function as a target component concentration meter, and therefore the actual CO2 concentration, from which the influence of the moisture contained in the exhaust gas is removed, can be accurately measured.

Note that the present invention is not limited to the above-described embodiment.

For example, in the above-described embodiment, the heating mechanisms 41 and 42 are independent of each other; however, the present invention may be configured to heat all of the sampling lines 11 and 12 and the concentration measuring parts 21 and 22 with one heating mechanism.

Also, the heating mechanism 41 may be one that heats the infrared light source 6, optical filter 71, and optical detector 81.

Further, in the above-described embodiment, the NDIR analyzer used as the first concentration measuring part 21 is configured to have the function as a moisture concentration meter and the function as a target component concentration meter; however, the moisture concentration meter and the target component concentration meter may be separate analyzers.

Regarding the tracer method, in the above-described embodiment, the target component is CO2; however, the target component may be another component contained in the exhaust gas. Also, the present invention may be adapted to mix an inert component not contained in the exhaust gas, such as He, into the exhaust gas emitted from the exhaust pipe, and measure He concentrations before and after the dilution.

Further, in the above-described embodiment, the flow rate control part 103 is of the critical flow venturi type; however, the present invention may be adapted to use a critical flow orifice (CFO), constant volume pump, blower, or the like to control the flow rate. Still, further, the present invention may be adapted to provide a flowmeter to instantaneously measure the diluted exhaust gas flow rate Qmix.

Regarding the exhaust gas analyzing system 100, in the above-described embodiment, the system is based on the constant volume dilution sampling method; however, the system may be based on a bag mini-diluter method that collects part of exhaust gas to dilute the collected exhaust gas at a constant ratio.

Besides, it should be appreciated that the present invention is not limited to any of the above-described embodiments, but can be variously modified without departing from the scope thereof.

REFERENCE SIGNS LIST

201: Internal combustion engine
202: Exhaust pipe
101: Constant volume sampling apparatus
ML: Main flow path
1: Exhaust gas flowmeter
11: First sampling line
21: First concentration measuring part
12: Second sampling line
22: Second concentration measuring part
3: Arithmetic unit
41: First heating mechanism
42: Second heating mechanism

What is claimed is:

1. An exhaust gas flowmeter used for an exhaust gas dilution system that is provided with a main flow path through which exhaust gas emitted from an internal combustion engine flows, and a diluent gas flow path through which diluent gas for diluting the exhaust gas flows, the diluent gas flow path meeting the main flow path, the exhaust gas flowmeter comprising:

a first sampling line for, from an upstream side of a meeting point between the main flow path and the diluent gas flow path in the main flow path, sampling raw exhaust gas that is the exhaust gas before dilution;

a first concentration measuring part that is provided in the first sampling line to measure concentration of a predetermined target component contained in the raw exhaust gas;

a second sampling line for, from a downstream side of the meeting point in the main flow path, sampling diluted exhaust gas that is the exhaust gas after dilution;

a second concentration measuring part that is provided in the second sampling line to measure concentration of the predetermined target component contained in the diluted exhaust gas; and an arithmetic unit that, with use of first measured concentration of the predetermined target component obtained by the first concentration measuring part, second measured concentration of the predetermined target component obtained by the second concentration measuring part, and a diluted exhaust gas flow rate that is a flow rate of the diluted exhaust gas, calculates a raw exhaust gas flow rate that is a flow rate of the raw exhaust gas, wherein in a state where the first sampling line and the first concentration measuring part are heated, the first concentration measuring part measures the concentration of the predetermined target component contained in the raw exhaust gas.

2. The exhaust gas flowmeter according to claim 1, wherein in a state where the second sampling line and the second concentration measuring part are heated, the second concentration measuring part measures the concentration of the predetermined target component contained in the diluted exhaust gas.

3. The exhaust gas flowmeter according to claim 1, wherein the heated concentration measuring part comprises a moisture concentration meter that measures moisture concentrations in the exhaust gas, a target component concentration meter that measures moisture-influenced concentration that is concentration of the predetermined target component in the exhaust gas in a state of being influenced by moisture, and calculates the concentration of the predetermined target component contained in the exhaust gas as concentration that is the moisture-influenced concentration from which an influence of the moisture is removed with use of the moisture concentration.

4. An exhaust gas analyzing system using the exhaust gas flowmeter according to claim 1.

* * * * *